(12) United States Patent
Qu et al.

(10) Patent No.: US 12,332,263 B2
(45) Date of Patent: Jun. 17, 2025

(54) AUTOMATED STORAGE AND RETRIEVAL DEVICE FOR BIOLOGICAL SAMPLE

(71) Applicant: SHANGHAI ORIGINCELL BIOLOGICAL CRYO EQUIPMENT CO., LTD., Shanghai (CN)

(72) Inventors: Jianguo Qu, Shanghai (CN); Sheng Qiao, Shanghai (CN)

(73) Assignee: SHANGHAI ORIGINCELL BIOLOGICAL CRYO EQUIPMENT CO., LTD., Shanghai (CN)

(*) Notice: Subject to any disclaimer, the term of this patent is extended or adjusted under 35 U.S.C. 154(b) by 0 days.

(21) Appl. No.: 19/015,785

(22) Filed: Jan. 10, 2025

(65) Prior Publication Data
US 2025/0147060 A1 May 8, 2025

Related U.S. Application Data

(63) Continuation of application No. PCT/CN2023/098022, filed on Jun. 2, 2023.

(30) Foreign Application Priority Data

Sep. 19, 2022 (CN) .................. 202222474434.8

(51) Int. Cl.
G01N 35/04 (2006.01)
G01N 35/00 (2006.01)
G01N 1/10 (2006.01)

(52) U.S. Cl.
CPC ....... *G01N 35/04* (2013.01); *G01N 35/00732* (2013.01); *G01N 2001/1081* (2013.01);
(Continued)

(58) Field of Classification Search
CPC ............ G01N 35/04; G01N 35/00732; G01N 2001/1081; G01N 2035/00752; G01N 2035/0406
See application file for complete search history.

(56) References Cited

U.S. PATENT DOCUMENTS 8,176,747 B2 * 5/2012 Howard .................. G01N 1/42
62/337
2024/0131689 A1 * 4/2024 Cunrath .................. B25J 9/046

FOREIGN PATENT DOCUMENTS

CN 108770835 A 11/2018
CN 209023566 U * 6/2019 ............... B65G 1/04
(Continued)

*Primary Examiner* — John McGuirk
(74) *Attorney, Agent, or Firm* — Bayramoglu Law Offices LLC

(57) ABSTRACT

An automated storage and retrieval device for a biological sample is provided. The automated storage and retrieval device includes an upper cabin and a liquid nitrogen storage tank, where the upper cabin is communicated with the liquid nitrogen storage tank through a storage and retrieval channel; the upper cabin is provided therein with an operation area; the operation area is provided with a rack gripping mechanism, a rack barcode scanning mechanism, a cryotube suction mechanism, and a cryotube barcode scanning mechanism, and is configured to retrieve and store samples from the liquid nitrogen storage tank in the upper cabin through the storage and retrieval channel; and the upper cabin is provided with a pressure relief member for automatically discharging a pressure of the upper cabin.

15 Claims, 12 Drawing Sheets

(52) U.S. Cl.
CPC .............. *G01N 2035/00752* (2013.01); *G01N 2035/0406* (2013.01)

(56) References Cited

FOREIGN PATENT DOCUMENTS

| | | | | |
|---|---|---|---|---|
| CN | 112938105 A | * | 6/2021 | ........... A01N 1/0268 |
| CN | 113115765 A | | 7/2021 | |
| CN | 218143685 U | | 12/2022 | |
| DE | 102016124723 A1 | | 6/2018 | |
| JP | 2017013957 A | | 1/2017 | |

\* cited by examiner

AUTOMATED STORAGE AND RETRIEVAL DEVICE FOR BIOLOGICAL SAMPLE

CROSS-REFERENCE TO THE RELATED APPLICATIONS

This application is a continuation application of International Application No. PCT/CN2023/098022, filed on Jun. 2, 2023, which is based upon and claims priority to Chinese Patent Application No. 202222474434.8, filed on Sep. 19, 2022, the entire contents of which are incorporated herein by reference.

TECHNICAL FIELD

The present disclosure relates to an automated storage and retrieval device for a biological sample, and belongs to the technical field of biological sample storage.

BACKGROUND

In existing automated storage and retrieval devices for biological samples, most non-ultra-large storage devices adopt a combined structure including a storage and retrieval mechanism and a liquid nitrogen low-temperature storage mechanism arranged in a centralized manner, such as a known low-temperature storage device for a biological sample (CN113115765A) and a known cooling and storage integrated device for a biological sample (CN209023566U).

The non-ultra-large storage devices in the prior art suffer from problems such as insufficient compactness of the storage and retrieval mechanism, limited storage capacity of cryotubes, and low automation and efficiency of docking between multiple storage devices. In addition, the upper cover of the existing non-ultra-large storage device is relatively bulky and opened manually. Especially in cryogenic storage environments, the upper cover will freeze on the tank body, causing inconvenience in opening the upper cover. Moreover, as the mounting platform for the storage and retrieval mechanism, the upper cover requires a certain degree of flatness. However, it is not convenient to perform mounting leveling of the upper cover and the tank body. Furthermore, the pressure relief function of the operation cabin/upper cabin of the storage and retrieval mechanism is imperfect, and a pressure relief valve is needed, which increases the cost.

SUMMARY

An objective of the present disclosure is to provide an automated storage and retrieval device for a biological sample. The present disclosure realizes the pressure relief function of the upper cabin, reasonably arranges various mechanisms for storage and retrieval, increases the storage capacity of cryotube, achieves efficient transport between multiple sample storage devices, and realizes an upper cover that is easy to open and level.

In order to solve the above technical problem, the present disclosure adopts the following technical solution.

An automated storage and retrieval device for a biological sample includes an upper cabin and a liquid nitrogen storage tank, where the upper cabin is communicated with the liquid nitrogen storage tank through a storage and retrieval channel; the upper cabin is provided therein with an operation area; the operation area is provided with a rack gripping mechanism, a rack barcode scanning mechanism, a cryotube suction mechanism, and a cryotube barcode scanning mechanism, and is configured to retrieve and store samples from the liquid nitrogen storage tank in the upper cabin through the storage and retrieval channel; and the upper cabin is provided with a pressure relief member for automatically discharging a pressure of the upper cabin.

Preferably, the pressure relief member includes a soft pressure relief tube; and the soft pressure relief tube includes one end communicated with the operation area and the other end closed by an adjusting element, with a closing size adjusted by an adjusting bolt group.

Preferably, the upper cabin includes a cabin base plate and an outer cabin cover provided on the cabin base plate; the outer cabin cover includes an operation chamber housing located above the storage and retrieval channel; and the pressure relief member is provided on the operation chamber housing.

Preferably, the outer cabin cover further includes an electrical control box housing provided side by side with the operation chamber housing on the cabin base plate and communicated with the operation chamber housing at a bottom.

Preferably, the rack gripping mechanism, the rack barcode scanning mechanism, the cryotube suction mechanism, and the cryotube barcode scanning mechanism are provided in the operation area through a reference plate; the reference plate is located on the cabin base plate; and the reference plate and the cabin base plate are jointly provided with a storage and retrieval port corresponding to the storage and retrieval channel; and the rack gripping mechanism is located at one side of the storage and retrieval port through a Y-axis moving mechanism; the other side of the storage and retrieval port is provided with the cryotube suction mechanism; and the rack barcode scanning mechanism and the cryotube barcode scanning mechanism are located at an end of the storage and retrieval port away from the electrical control box housing.

Preferably, the rack gripping mechanism includes a gripper, a driving actuator, a lifting slider, and a longitudinal slide rail; the gripper is provided on the lifting slider through a connecting plate; and the lifting slider is slidably provided on the longitudinal slide rail and is connected to the driving actuator in a transmission manner; and the Y-axis moving mechanism includes a Y-axis track and a moving carriage slidably connected to the Y-axis track; the Y-axis track is fixed to the reference plate; and the longitudinal slide rail is connected to the moving carriage.

Preferably, the cryotube suction mechanism includes a driving motor, a vertical rod, a slider, a rotating arm, and a suction mechanism; and the suction mechanism is provided on the slider through the rotating arm; and the slider is slidably provided on a slide rail of the vertical rod and is connected to the driving motor in a transmission manner.

Preferably, the suction mechanism includes a suction tip, a pedestal, a base, an air rod, a magnetic induction coil, and a magnetic rod; the base is connected to the rotating arm; the pedestal is connected to the base through a fixed plate; the air rod includes an upper end connected to the pedestal and a lower end provided with the suction tip and extending through a first through hole of the base towards a lower side of the rotating arm; and the magnetic rod includes an upper end connected to the pedestal and a lower end extending into a second through hole of the base through the magnetic induction coil; and a liquid storage cylinder and a cooling guide tube that are communicated vertically and hold liquid nitrogen are sleeved outside the air rod.

Preferably, the rack barcode scanning mechanism includes a rack barcode scanning fixed frame provided on the reference plate; an upper opening of the rack barcode scanning fixed frame is provided with a rack barcode scanning upper cover plate; the rack barcode scanning upper cover plate is provided with a light source element and a barcode scanning window; and the rack barcode scanning fixed frame is provided therein with an intelligent barcode scanner that faces the barcode scanning window.

Preferably, the cryotube barcode scanning mechanism includes a barcode scanning motor provided on the reference plate; the barcode scanning motor is connected to a rotating post in a driving manner; a side of the rotating post is fixedly connected to a rotary arm; and the rotary arm is provided with an intelligent barcode reader.

Preferably, the liquid nitrogen storage tank includes a tank body and an upper cover; the upper cover includes an upper support portion and a lower connection portion that are integrated and respectively configured to mount the upper cabin and connect an upper opening of the tank body in a sealing manner; and the storage and retrieval channel is located on the upper cover and penetrates through the upper support portion and the lower connection portion.

Preferably, a bottom of the tank body is provided on a support seat, and four sides of the tank body are fixed by a support frame; and the upper support portion of the upper cover extends below an outer periphery of the lower connection portion, and is supported by a leveling alignment post provided at a top of the support frame.

Preferably, the tank body includes an inner tank and an outer tank sleeved outside the inner tank; the inner tank is provided therein with a cellular turntable assembly; and a cryotube is stored on the cellular turntable assembly through an aluminum tube; and an upper side of the cellular turntable assembly is connected to a fixed plate; the fixed plate is provided with a picked cryotube temporary storage plate; the picked cryotube temporary storage plate is rotatable with the cellular turntable assembly to the storage and retrieval channel; and the picked cryotube temporary storage plate includes a temporary storage plate as well as a rack storage hole and a cryotube temporary storage hole provided on the temporary storage plate.

Preferably, a guide rail type transfer tank sample transport mechanism is provided outside the liquid nitrogen storage tank; the cabin base plate and the reference plate share an extension portion beyond the upper cover; the extension portion is provided with a channel opening and located above the guide rail type transfer tank sample transport mechanism; and an opening mechanism is provided on the reference plate at a side of the channel opening.

Preferably, the opening mechanism includes an opening plate that is provided therein with a magnetic attraction element; the opening plate is connected to an upper end of a second movable link; a lower end of the second movable link is slidably provided in a movable frame at one end of a first movable link through a movable element; the other end of the first movable link is hinged to a support; and the support is fixed to the reference plate; and the second movable link is further connected to a lifting drive element through a rotating shaft; the lifting drive element is provided with a limit element for constraining a movement angle of the second movable link; the lifting drive element is further provided on a support rail of the support through a sliding element; and the sliding element is driven by an opening motor to move up and down.

Preferably, the guide rail type transfer tank sample transport mechanism includes a transfer tank transport mechanism and a lifting mechanism; and the transfer tank transport mechanism is provided at a top of the lifting mechanism through a transfer guide rail; and a transfer tank enters the channel opening through the lifting mechanism; and alternatively, the transfer tank is placed onto the transfer tank transport mechanism, and docked by the transfer tank transport mechanism along a guide rail to another automated storage and retrieval device for a biological sample connected in series.

Preferably, the transfer tank transport mechanism includes a transport housing and a carrier pedestal that are connected vertically; the transport housing is provided with a support plate for placing the transfer tank; and the carrier pedestal is provided on the transfer guide rail; and the lifting mechanism includes a support member and a driving member that are connected to a side of the liquid nitrogen storage tank; and the support member is fixed to the transfer guide rail from a bottom and able to drive the transfer tank to move up and down under the control of the driving member.

The above technical solution of the present disclosure has the following beneficial effects:

The upper cabin is provided therein with an operation area including a rack gripping mechanism, a rack barcode scanning mechanism, a cryotube suction mechanism, and a cryotube barcode scanning mechanism. Samples from the liquid nitrogen storage tank are retrieved and stored in the upper cabin through a storage and retrieval channel. The design achieves a compact structure. The upper cabin is provided with a pressure relief member, which realizes a pressure relief function, has low cost, and can automatically discharge the pressure in the upper cabin.

Figure 1:
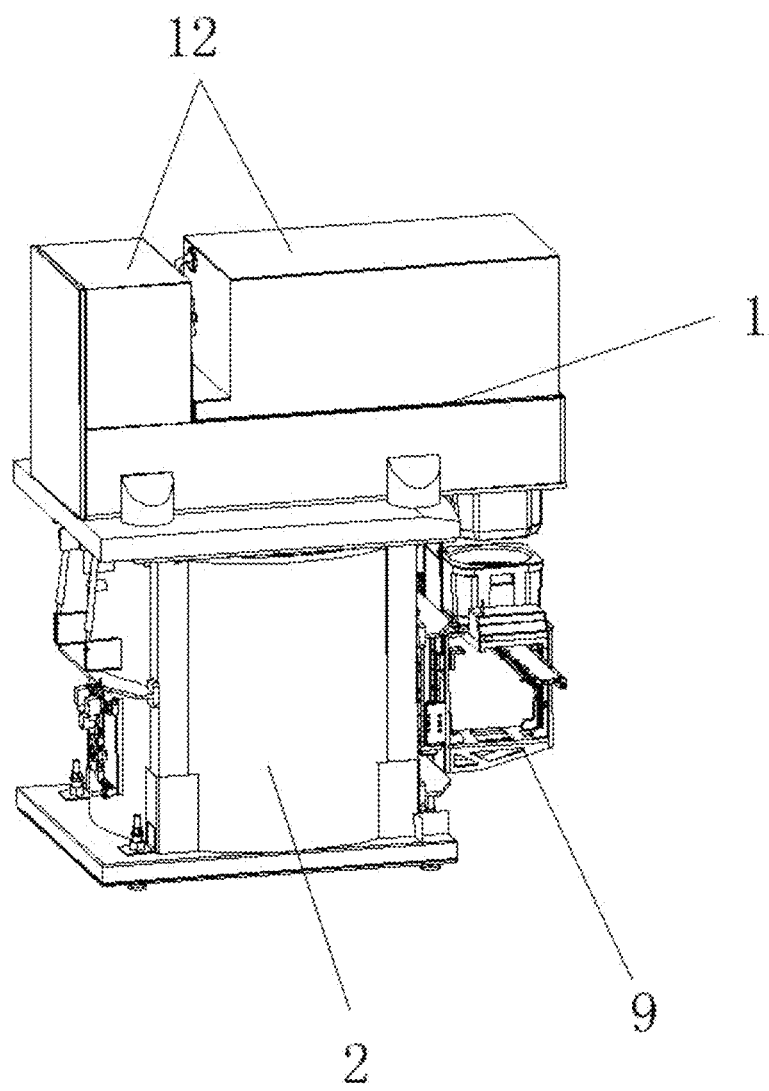
FIG. 1 is a stereoscopic view of an automated storage and retrieval device for a biological sample according to the present disclosure.
Figure 2:
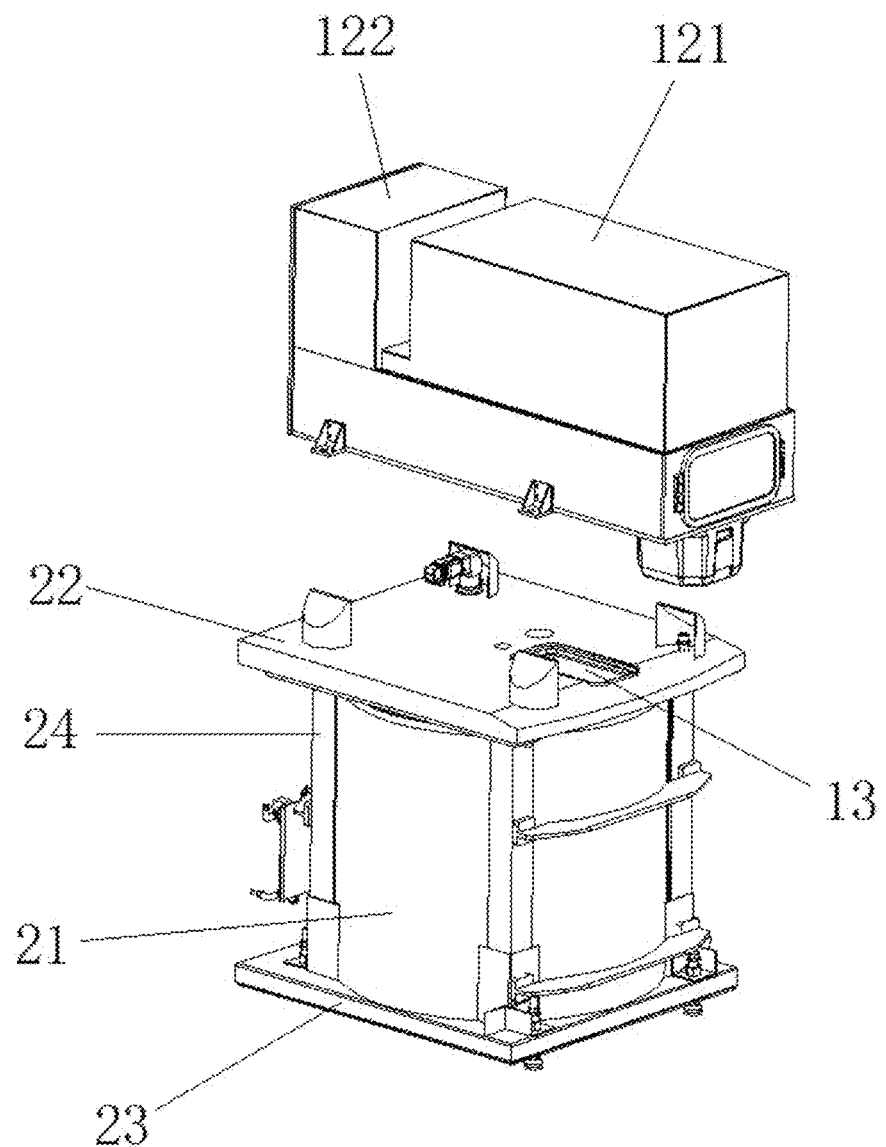
FIG. 2 is an exploded view of the automated storage and retrieval device for a biological sample according to the present disclosure.
Figure 3:
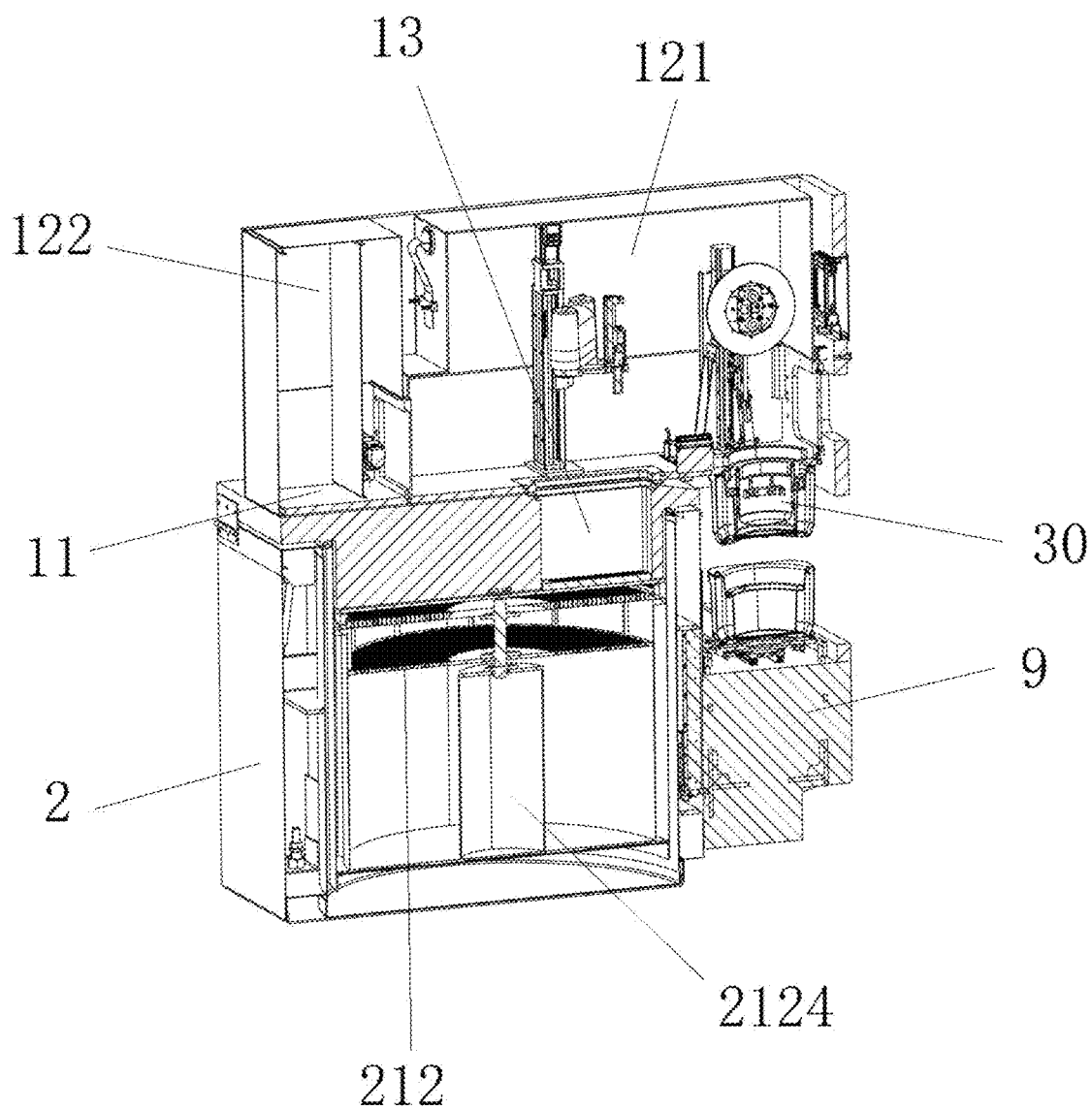
FIG. 3 is a sectional view of the automated storage and retrieval device for a biological sample according to the present disclosure.
Figure 4:
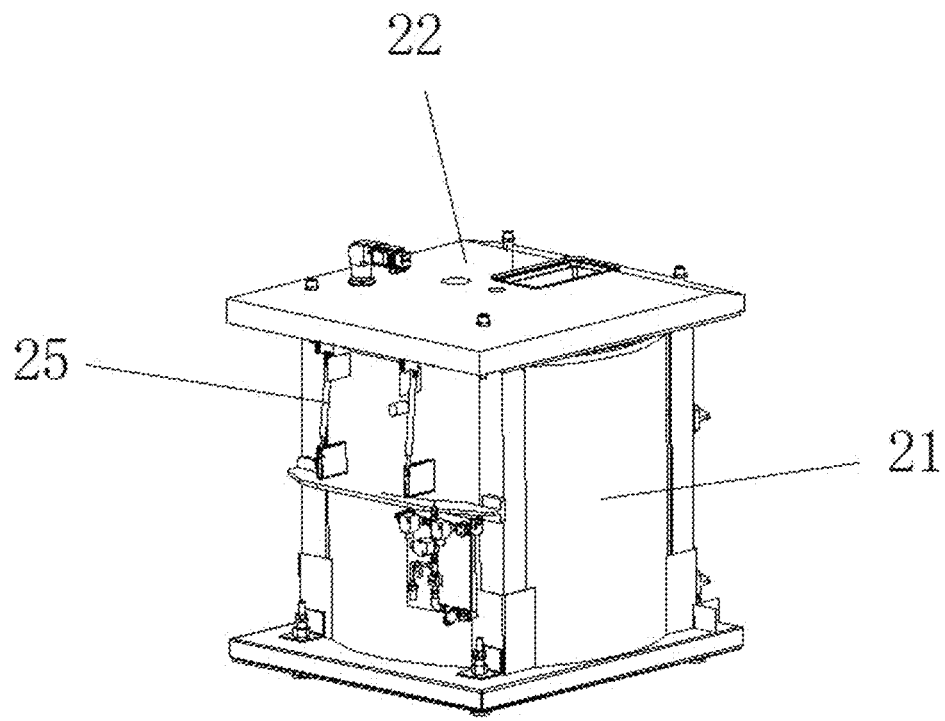
FIG. 4 is a stereoscopic view of a liquid nitrogen storage tank of the automated storage and retrieval device for a biological sample according to the present disclosure.
Figure 5:
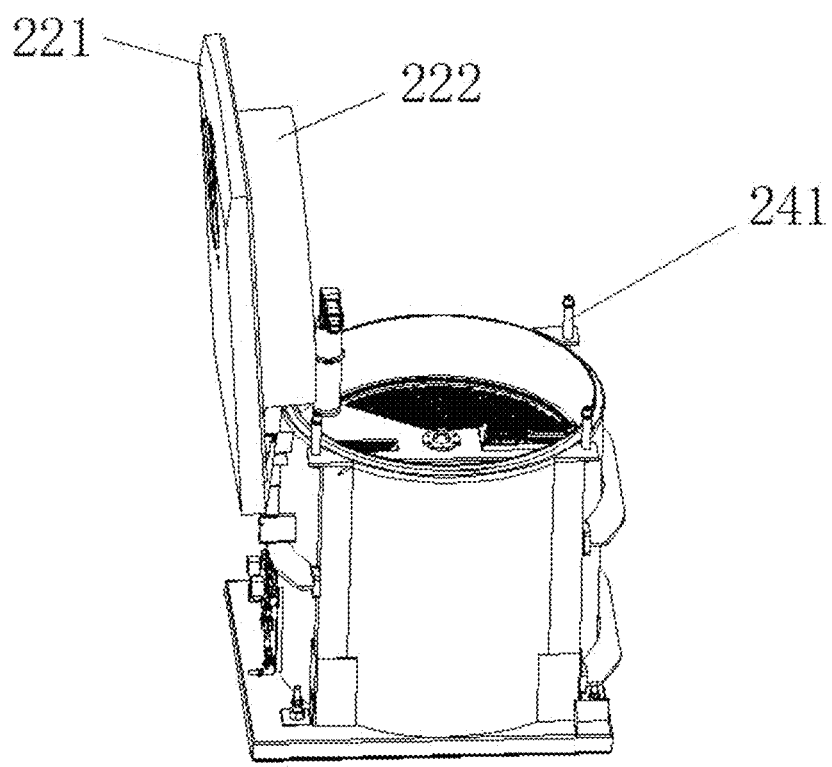
FIG. 5 is a stereoscopic view of the liquid nitrogen storage tank, in an open state, of the automated storage and retrieval device for a biological sample according to the present disclosure.
Figure 6:
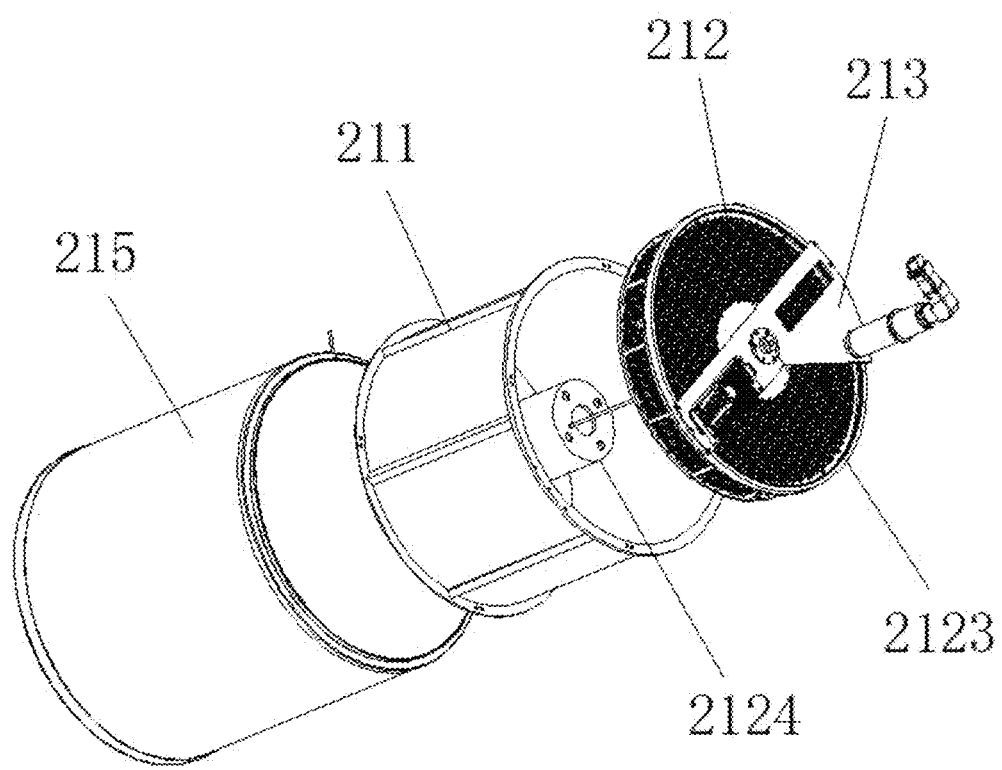
FIG. 6 is an exploded view of an internal structure of the liquid nitrogen storage tank of the automated storage and retrieval device for a biological sample according to the present disclosure.
Figure 7:
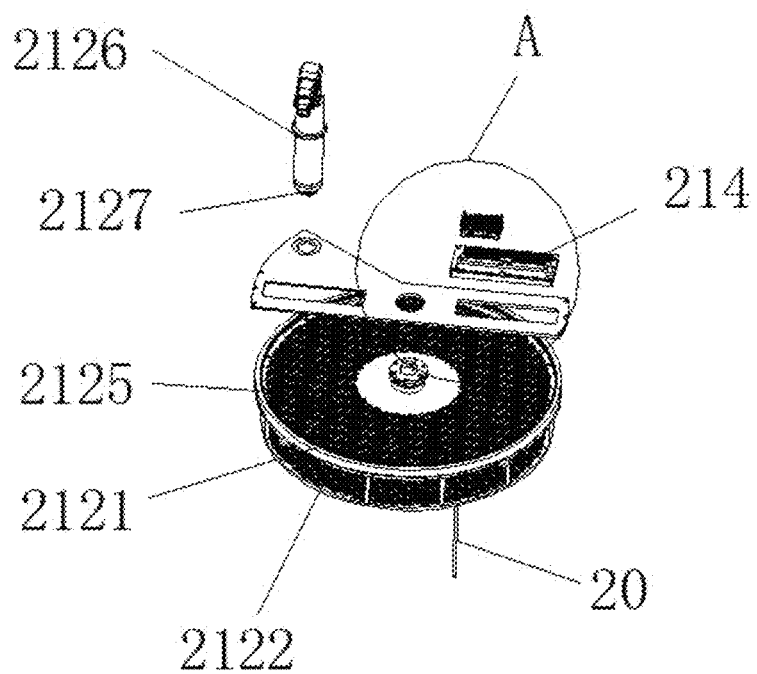
FIG. 7 is an exploded view of a part of the structure shown in FIG. 6.
Figure 8:
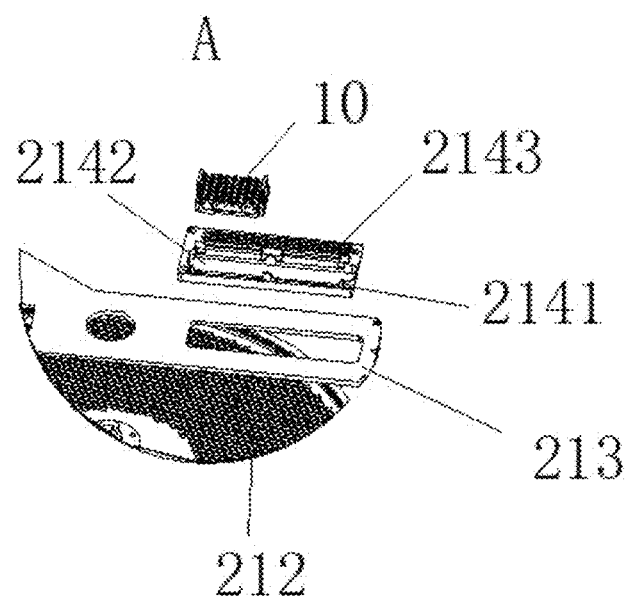
FIG. 8 is an enlarged view of A shown in FIG. 7.
Figure 9:
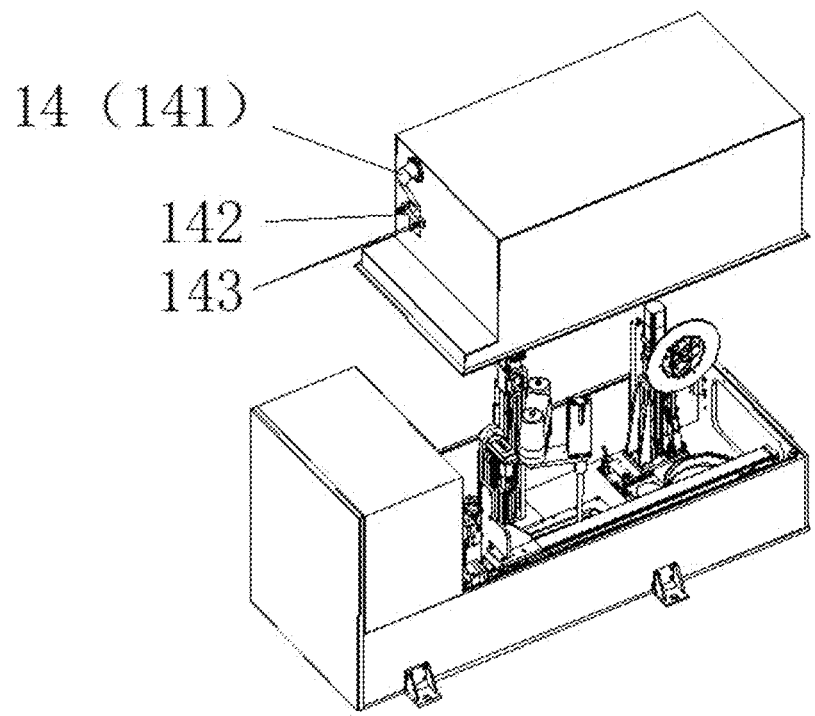
FIG. 9 is a partial exploded view of an upper cabin of the automated storage and retrieval device for a biological sample according to the present disclosure.
Figure 10:
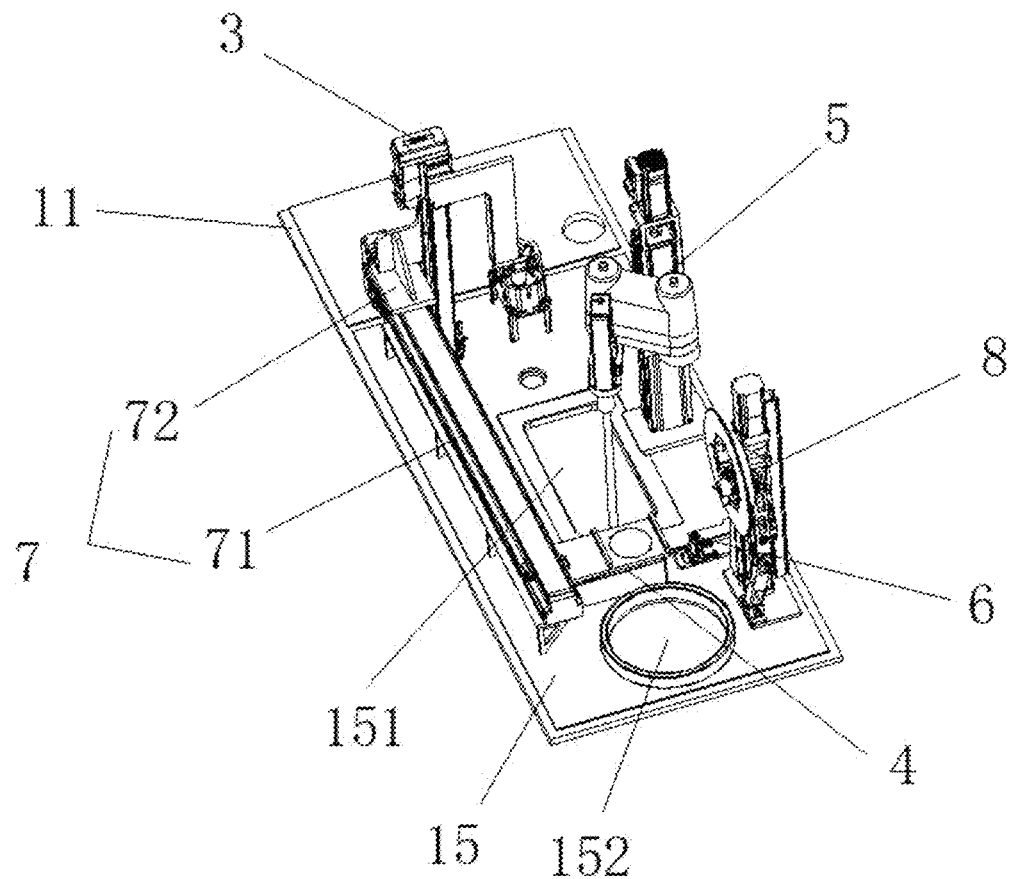
FIG. 10 is an internal structural diagram of the upper cabin of the automated storage and retrieval device for a biological sample according to the present disclosure.
Figure 11:
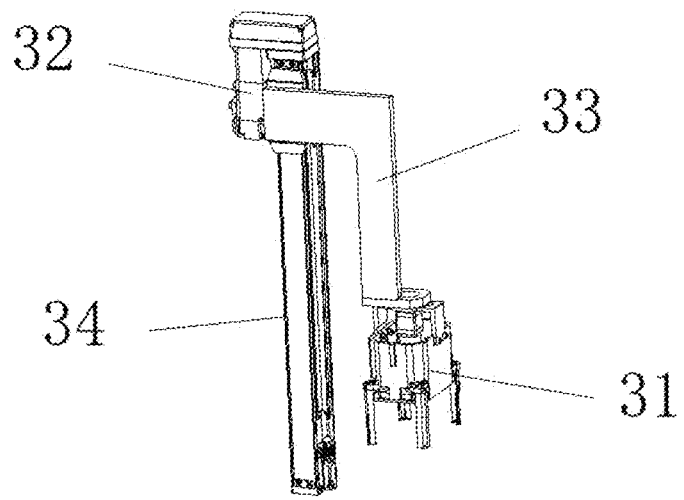
FIG. 11 is a stereoscopic view of a rack gripping mechanism of the automated storage and retrieval device for a biological sample according to the present disclosure.
Figure 12:
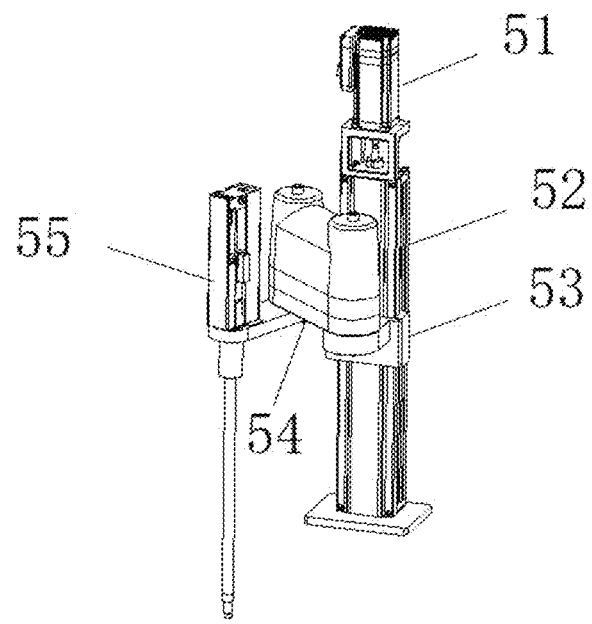
FIG. 12 is a stereoscopic view of a cryotube suction mechanism of the automated storage and retrieval device for a biological sample according to the present disclosure.
Figure 13:
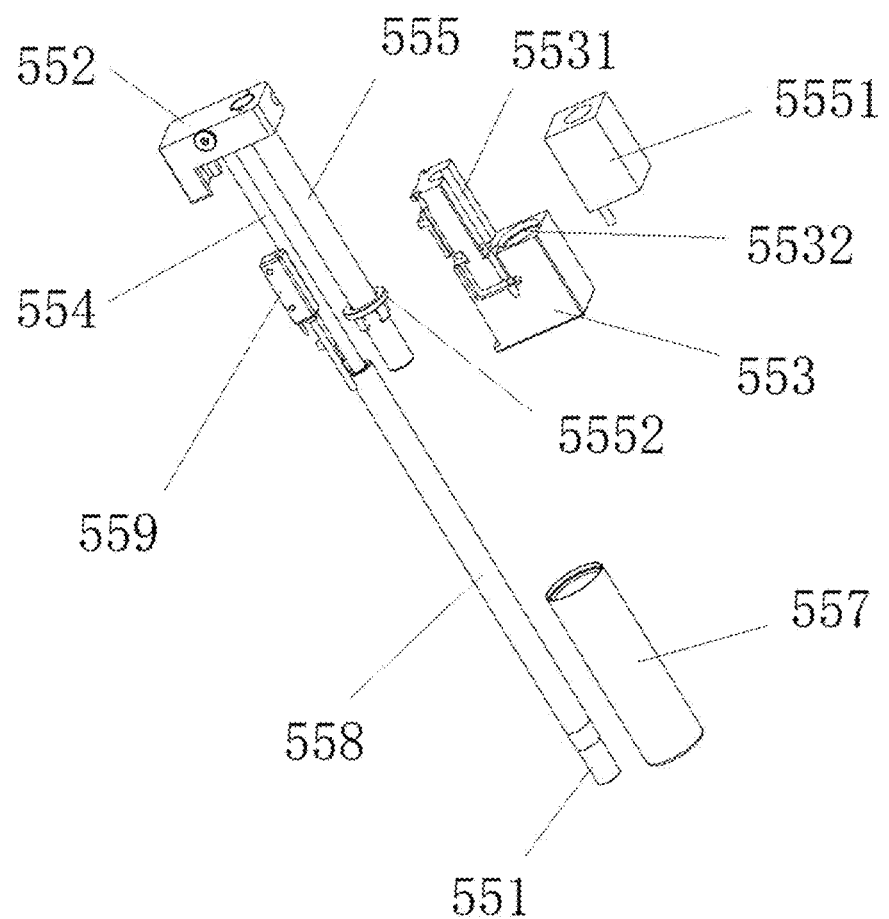
FIG. 13 is an exploded view of the cryotube suction mechanism of the automated storage and retrieval device for a biological sample according to the present disclosure.
Figure 14:
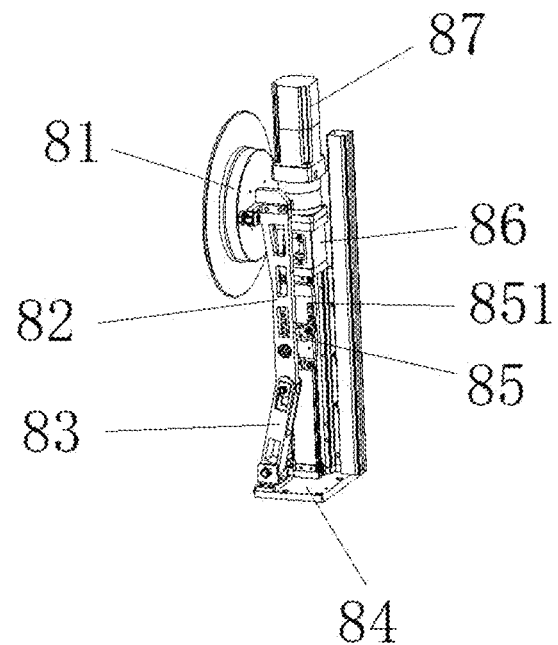
FIG. 14 is a stereoscopic view of an opening mechanism of the automated storage and retrieval device for a biological sample according to the present disclosure.
Figure 15:
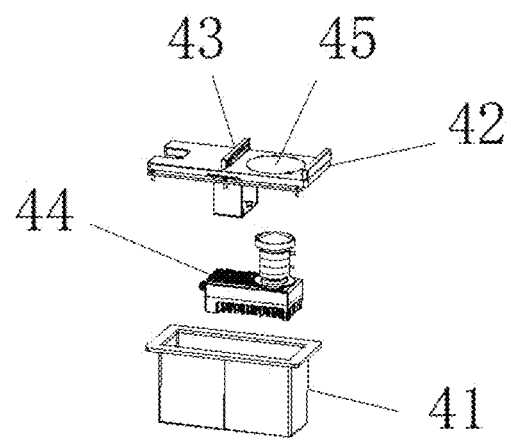
FIG. 15 is a stereoscopic view of a rack barcode scanning mechanism of the automated storage and retrieval device for a biological sample according to the present disclosure.
Figure 16:
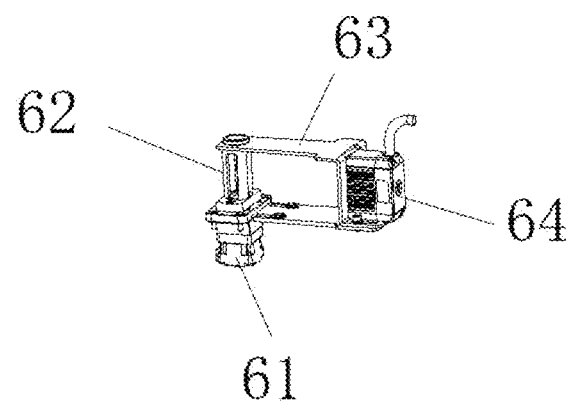
FIG. 16 is a stereoscopic view of a cryotube barcode scanning mechanism of the automated storage and retrieval device for a biological sample according to the present disclosure.
Figure 17:
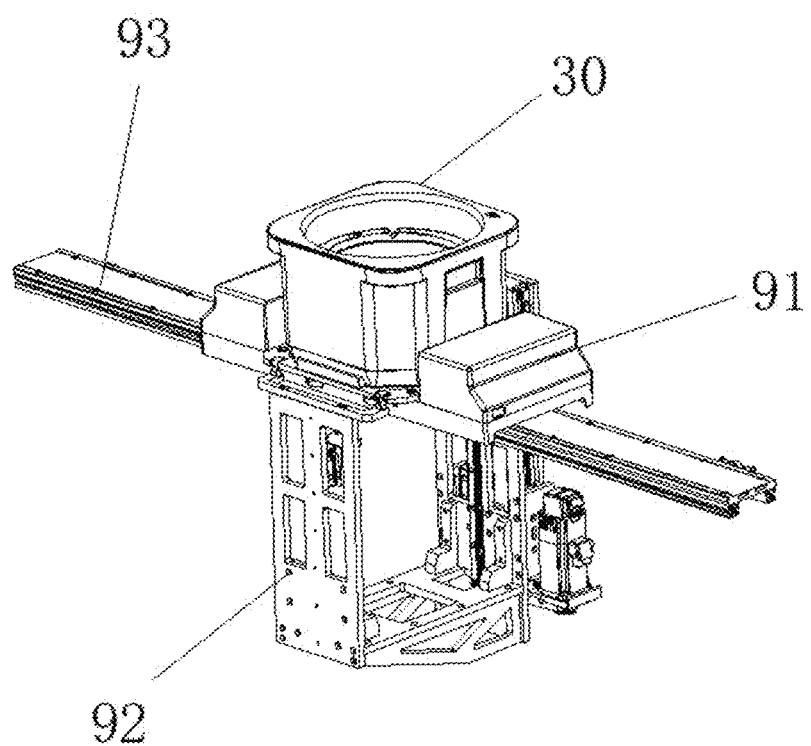
FIG. 17 is a stereoscopic view of a guide rail type transfer tank sample transport mechanism of the automated storage and retrieval device for a biological sample according to the present disclosure.
Figure 18:
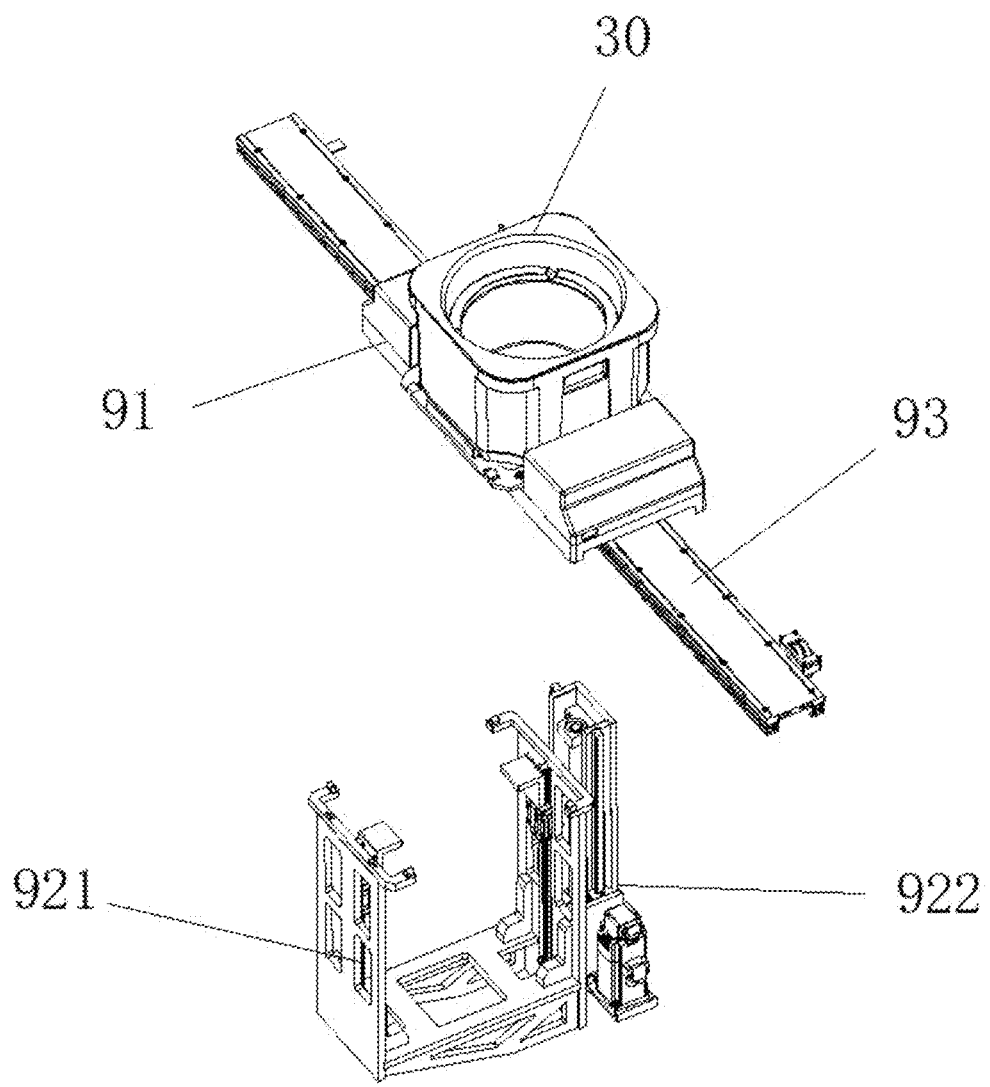
FIG. 18 is an exploded view of the guide rail type transfer tank sample transport mechanism of the automated storage and retrieval device for a biological sample according to the present disclosure.
Figure 19:
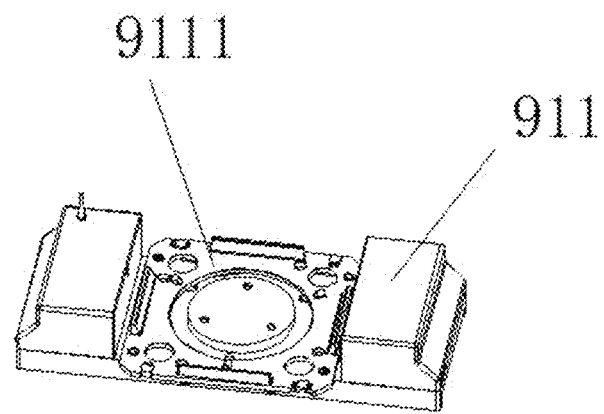
FIG. 19 is a stereoscopic view of a transport housing of a transfer tank transport mechanism of the automated storage and retrieval device for a biological sample according to the present disclosure.
Figure 20:
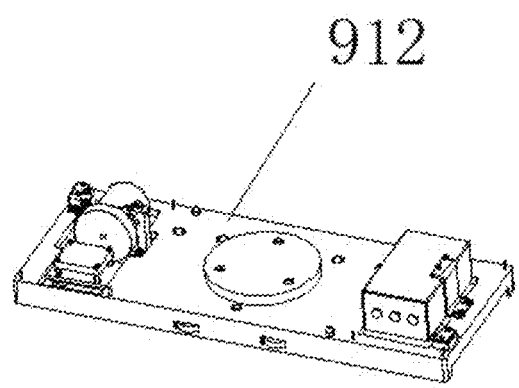
FIGS. 20 and 21 are respectively top and bottom views of a carrier pedestal of the transfer tank transport mechanism of the automated storage and retrieval device for a biological sample according to the present disclosure.
Figure 21:
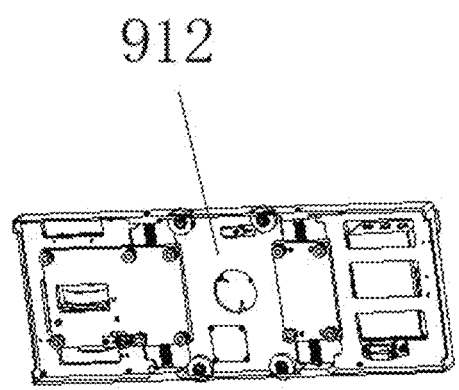

REFERENCE NUMERALS 10. rack; 20. aluminum tube; and 30. transfer tank;
1. upper cabin; 11. cabin base plate; 12. outer cabin cover; 121. operation chamber housing; 122. electrical control box housing; 13. storage and retrieval channel; 14. pressure relief member; 141. soft pressure relief tube; 142. adjusting element; 143. adjusting bolt group; 15. reference plate; 151. storage and retrieval port; and 152. channel opening;
2. liquid nitrogen storage tank; 21. tank body; 211. inner tank; 212. cellular turntable assembly; 2121. upper cellular plate; 2122. lower cellular plate; 2123. rotating shaft; 2124. cold insulation inner tank; 2125. transmission gear ring; 2126. rotating motor; 2127. driving gear; 213. fixed plate; 214. picked cryotube temporary storage plate; 2141. temporary storage plate; 2142. rack storage hole; 2143. cryotube temporary storage hole; 215. outer tank; 22. upper cover; 221. upper support portion; 222. lower connection portion; 23. support seat; 24. support frame; 241. leveling alignment post; and 25. connecting element;
3. rack gripping mechanism; 31. gripper; 32. driving actuator; 33. lifting slider; and 34. longitudinal slide rail;
4. rack barcode scanning mechanism; 41. rack barcode scanning fixed frame; 42. rack barcode scanning upper cover plate; 43. light source element; 44. intelligent barcode scanner; and 45. barcode scanning window;
5. cryotube suction mechanism; 51. driving motor; 52. vertical rod; 53. slider; 54. rotating arm; 55. suction mechanism; 551. suction tip; 552. pedestal; 553. base; 5531. first through hole; 5532. second through hole; 554. air rod; 555. magnetic rod; 5551. magnetic induction coil; 5552. damping ring. side fixed plate; 557. liquid storage cylinder; 558. cooling guide tube; and 559. sensor;
6. cryotube barcode scanning mechanism; 61. barcode scanning motor; 62. rotating post; 63. rotary arm; and 64. intelligent barcode reader;
7. Y-axis moving mechanism; 71. Y-axis track; and 72. moving carriage;
8. opening mechanism; 81. opening plate; 82. second movable link; 83. first movable link; 84. support; 85. lifting drive element; 851. limit element; 86. sliding element; and 87. opening motor; and
9. guide rail type transfer tank sample transport mechanism; 91. transfer tank transport mechanism; 911. transport housing; 9111. support plate; 912. carrier pedestal; 92. lifting mechanism; 921. support member; 922. driving member; and 93. transfer guide rail.

DETAILED DESCRIPTION OF THE EMBODIMENTS

The technical solution of the present disclosure is described in further detail below with reference to embodiments and drawings.

An automated storage and retrieval device for a biological sample includes upper cabin 1 and liquid nitrogen storage tank 2. The upper cabin 1 is communicated with the liquid nitrogen storage tank 2 through storage and retrieval channel 13. The upper cabin 1 is provided therein with an operation area. The operation area is provided with rack gripping mechanism 3, rack barcode scanning mechanism 4, cryotube suction mechanism 5, and cryotube barcode scanning mechanism 6, and is configured to retrieve and store samples from the liquid nitrogen storage tank 2 in the upper cabin 1 through the storage and retrieval channel 13. The upper cabin 1 is provided with pressure relief member 14 for automatically discharging a pressure of the upper cabin 1.

In a further implementation of the present disclosure, the pressure relief member 14 includes soft pressure relief tube 141, such as a rubber tube. The soft pressure relief tube 141 includes one end communicated with the operation area and the other end closed by an adjusting element 142, with a closing size adjusted by adjusting bolt group 143.

The pressure relief method of the soft pressure relief tube 141 reduces costs and can automatically discharge the pressure of the upper cabin 1. Specifically, the height of the adjusting element 142 is manually adjusted to preset, increase or decrease the pressure relief amount. The adjusting element 142 cannot completely squeeze the soft pressure relief tube 141. Therefore, when the pressure inside the upper cabin 1 is too high, it is automatically discharged through the soft pressure relief tube 141.

In a further implementation of the present disclosure, the upper cabin 1 includes cabin base plate 11 and outer cabin cover 12 provided on the cabin base plate 11. The outer cabin cover 12 includes operation chamber housing 121 located above the storage and retrieval channel 13. The pressure relief member 14 is provided on the operation chamber housing 121.

In a specific implementation, the soft pressure relief tube 141 can be provided between a pair of adjusting elements 142. The pair of adjusting elements 142 includes a fixed adjusting element and a movable adjusting element. The fixed adjusting element is connected to the operation chamber housing 121, and the movable adjusting element 142 is configured to adjust a spacing through the adjusting bolt group 143 connected between the fixed adjusting element and the movable adjusting element, achieving different squeezing effects on the soft pressure relief tube 141. Specifically, the adjusting bolt group 143 includes an adjusting bolt and a reset bolt. The adjusting bolt includes a bolt rod and a bolt cap. The adjusting element 142 is provided on the bolt rod to adjust the spacing by twisting the bolt cap. The reset bolt includes a bolt rod and a spring fitted onto the bolt rod. The adjusting element 142 is also provided on the bolt rod of the reset bolt. The springs on the bolt rods constrain the adjusting elements 142 on an outer side to approach each other or the mounting position under an elastic force to achieve a reset effect, thereby adapting to the changing pressure relief requirements. In another alternative structural solution, the soft pressure relief tube 141 is located below one of the adjusting elements 142. The adjusting element 142 is connected to the operation chamber housing 121 through the adjusting bolt group 143. The adjusting bolt group 143 is operated to change the height of the adjusting element 142, thereby achieving different squeezing effects and pressure relief amounts.

A space enclosed by the outer cabin cover 12 and the cabin base plate 11 forms the operation area, which is configured to achieve the storage and retrieval of rack 10 or cryotubes in a low-temperature environment.

In a further implementation of the present disclosure, the outer cabin cover 12 further includes electrical control box housing 122 provided side by side with the operation chamber housing 121 on the cabin base plate 11 and communicated with the operation chamber housing at a bottom.

The electrical control box housing 122 is provided therein with electrical elements required for various structural functions of the rack gripping mechanism 3, the rack barcode scanning mechanism 4, the cryotube suction mechanism 5, and the cryotube barcode scanning mechanism 6 in the operation chamber housing 121.

In order to further improve the intelligence level of sample storage and retrieval, in this embodiment, a controller and a valve assembly can also be provided, which can be mounted on the upper cabin 1 and the liquid nitrogen storage tank 2 and associated with other existing mechanisms or structures to achieve automation control.

In a further implementation of the present disclosure, the rack gripping mechanism 3, the rack barcode scanning mechanism 4, the cryotube suction mechanism 5, and the cryotube barcode scanning mechanism 6 are provided in the operation area through reference plate 15. The reference plate 15 is located on the cabin base plate 11, and the reference plate and the cabin base plate are jointly provided with storage and retrieval port 151 corresponding to the storage and retrieval channel 13.

The rack gripping mechanism 3 is located at one side of the storage and retrieval port 151 through Y-axis moving mechanism 7. The other side of the storage and retrieval port is provided with the cryotube suction mechanism 5. The rack barcode scanning mechanism 4 and the cryotube barcode scanning mechanism 6 are located at an end of the storage and retrieval port 151 away from the electrical control box housing 122.

The rack 10 with cryotubes is gripped by the rack gripping mechanism 3. Firstly, in the upper cabin 1, the rack barcode scanning mechanism 4 scans and enters information. Then, the rack 10 is moved into rack storage hole 2142 in the liquid nitrogen storage tank 2 to achieve whole-process cold chain cryotube picking. The cryotube suction mechanism 5 withdraws the cryotube from the rack 10 and temporarily places the cryotube into the cryotube temporary storage hole. Then the cryotube is lifted into the operation area, and the information of the cryotube is scanned and entered through the cryotube barcode scanning mechanism 6. Afterwards, the cryotube is stored into aluminum tube 20 of cellular turntable assembly 212.

The reference plate 15 provides a good platform for the mounting of various functional mechanisms. The overall layout structure centered on the storage and retrieval port 151 is compact and reasonable, well meeting the requirements of non-ultra-large storage devices.

In a further implementation of the present disclosure, the rack gripping mechanism 3 includes gripper 31, driving actuator 32, lifting slider 33, and longitudinal slide rail 34. The gripper 31 is provided on the lifting slider 33 through a connecting plate. The lifting slider 33 is slidably provided on the longitudinal slide rail 34 and is connected to the driving actuator 32 in a transmission manner.

The Y-axis moving mechanism 7 includes Y-axis track 71 and moving carriage 72 slidably connected to the Y-axis track. The Y-axis track 71 is fixed to the reference plate 15. The longitudinal slide rail 34 is connected to the moving carriage 72.

In a further implementation of the present disclosure, the cryotube suction mechanism 5 includes driving motor 51, vertical rod 52, slider 53, rotating arm 54, and suction mechanism 55.

The suction mechanism 55 is provided on the slider 53 through the rotating arm 54. The slider 53 is slidably provided on a slide rail of the vertical rod 52 and is connected to the driving motor 51 in a transmission manner.

In a further implementation of the present disclosure, the suction mechanism 55 includes suction tip 551, pedestal 552, base 553, air rod 554, magnetic induction coil 5551, and magnetic rod 555. The base 553 is connected to the rotating arm 54. The pedestal 552 is connected to the base 553 through side fixed plate. An upper end of the air rod 554 is connected to the pedestal 552. A lower end of the air rod is provided with the suction tip 551 and extends through first through hole 5531 of the base 553 towards a lower side of the rotating arm 54. An upper end of the magnetic rod 555 is connected to pedestal 552 and communicated with the air rod (not shown in the figure). A lower end of the magnetic rod passes through the magnetic induction coil 5551 and extends into second through hole 5532 of the base 553. A lower end of the magnetic induction coil 5551 is inserted into the second through hole 5532. Cooling guide tube 558 is sleeved outside the suction tip 551. An outer periphery of the cooling guide tube 558 is nested inside liquid storage cylinder 557 that holds liquid nitrogen to realize cold insulation of the suction tip 551 during a process of sucking the cryotube.

Furthermore, the suction mechanism 55 may also include sensor 559 for detecting a rotation position and damping ring 5552 provided on the magnetic rod 555. The damping ring 5552 is sleeved on the magnetic rod 555 and extends through the magnetic induction coil 5551 with the magnetic rod 555 to the second through hole 5532. The rotation position refers to a rotation position of an X-axis where the suction mechanism 55 is located relative to a Y-axis where the rotating arm 54 is located.

The magnetic rod 555 cooperates with the magnetic induction coil 5551 to convert electrical energy into magnetic force for the air rod 554 to generate adsorption force, ultimately adsorbing the cryotube through the suction tip 551. In another alternative implementation, the magnetic rod 555 and related elements may not be provided. On the contrary, the upper end of the air rod 554 is communicated with a suction pump suction tube to enable the suction tip 551 to perform suction operation.

In a further implementation of the present disclosure, the rack barcode scanning mechanism 4 includes rack barcode scanning fixed frame 41 provided on the reference plate 15. An upper opening of the rack barcode scanning fixed frame 41 is provided with rack barcode scanning upper cover plate 42. The rack barcode scanning upper cover plate 42 is provided with light source element 43 and barcode scanning window 45. The rack barcode scanning fixed frame 41 is provided therein with intelligent barcode scanner 44 that faces the barcode scanning window 45. The barcode scanning window 45 can be provided with a transparent glass. The light source element 43 serves as a supplementary light source.

In a further implementation of the present disclosure, the cryotube barcode scanning mechanism 6 includes barcode scanning motor 61 provided on the reference plate 15. The barcode scanning motor 61 is connected to the rotating post 62 in a driving manner. A side of the rotating post 62 is fixedly connected to the rotary arm 63. The rotary arm 63 is provided with intelligent barcode reader 64.

In a further implementation of the present disclosure, the liquid nitrogen storage tank 2 includes tank body 21 and upper cover 22. The upper cover 22 includes upper support portion 221 and lower connection portion 222 that are integrated and respectively configured to mount the upper cabin 1 and connect an upper opening of the tank body 21 in a sealing manner. The storage and retrieval channel 13 is located on the upper cover 22 and penetrates through the upper support portion 221 and the lower connection portion 222.

Specifically, the tank body 21 and the upper cover 22 can be opened and closed in a relative rotation manner through connecting element 25 located at a side thereof. The connecting element 25 may include a rotating rod. Two ends of the rotating rod are hinged to the upper cover 22 and the tank body 21 respectively through connecting elements. The rotating rod can be an automatic or manual structure, such as existing electric rod or hydraulic rod, to achieve manual or automatic opening of the cover, facilitating the mounting or maintenance of inner tank 211.

In a further implementation of the present disclosure, a bottom of the tank body 21 is provided on support seat 23, and four sides of the tank body are fixed by support frame 24. The upper support portion 221 of the upper cover 22 extends below an outer periphery of the lower connection portion 222, and is supported by leveling alignment post 241 provided at a top of the support frame 24.

The leveling alignment post 241 matches the upper cover 22 with the upper support portion 221 and the lower connection portion 222, ensuring good sealing and cold insulation effects, and enabling mounting leveling.

In a further implementation of the present disclosure, the tank body 21 includes the inner tank 211 and outer tank 215 sleeved outside the inner tank. The inner tank 211 is provided therein with the cellular turntable assembly 212. The cryotube is stored on the cellular turntable assembly 212 through the aluminum tube 20.

An upper side of the cellular turntable assembly 212 is connected to fixed plate 213. The fixed plate 213 is provided with picked cryotube temporary storage plate 214. The picked cryotube temporary storage plate 214 is rotatable with the cellular turntable assembly 212 to the storage and retrieval channel 13. The picked cryotube temporary storage plate 214 includes temporary storage plate 2141 as well as rack storage hole 2142 and cryotube temporary storage hole 2143 provided on the temporary storage plate. The picked cryotube temporary storage plate 214 can be provided at a through hole of the fixed plate 213.

The cellular turntable assembly 212 may specifically include lower cellular plate 2122 and upper cellular plate 2121 arranged in parallel. Circumferences of the lower cellular panel 2122 and the upper cellular panel 2121 are combined together through a connecting post with cooling guide and support functions. The lower cellular plate 2122 and the upper cellular plate 2121 each are provided with cells. The aluminum tube 20 is stored into the cell to store the cryotube. A center of the lower cellular plate 2122, the upper cellular plate 2121, and the fixed plate 213 is provided with rotating shaft 2123. Cold insulation inner tank 2124 can be further provided below the rotating shaft 2123. An upper side of the cellular plate 2121 is fixedly provided with transmission gear ring 2125. The transmission gear ring 2125 is fixedly connected to the fixed plate 213. An inner side of the transmission ring gear 2125 is meshed with driving gear 2127. The driving gear 2127 is driven by rotating motor 2126, achieving rotation of the cellular turntable assembly 212. Such a cellular cryotube storage structure greatly increases the sample storage capacity.

Thanks to the design of the fixed plate 213 and the temporary storage plate 214, the storage and retrieval of the rack 10 and the cryotube is completed on the same component, achieving a compact structure that meets the requirements of non-ultra-large storage devices and cellular retrieval. The retrieval and picking of cryotubes can be carried out in the liquid nitrogen storage tank 2 in a low-temperature environment through the rack storage hole 2142 and the cryotube temporary storage hole 2143 of the picked cryotube temporary storage plate 214, ensuring the whole-process cold chain storage and retrieval of samples.

In a further implementation of the present disclosure, guide rail type transfer tank sample transport mechanism 9 is provided outside the liquid nitrogen storage tank 2. The cabin base plate 11 and the reference plate 15 share an extension portion beyond the upper cover 22. The extension portion is provided with channel opening 152 and located above the guide rail type transfer tank sample transport mechanism 9. Opening mechanism 8 is provided on the reference plate 15 at a side of the channel opening 152.

The storage process of transfer samples is as follows. Through the guide rail type transfer tank sample transport mechanism 9, transfer tank 30 is transferred from an automated storage and retrieval device for a biological sample to the retrieval position (below the channel opening 152) of an intended automated storage and retrieval device for a biological sample. The lifting mechanism 92 lifts the transfer tank 30 to the channel opening 152. The opening mechanism 8 opens a cover of the transfer tank 30. The rack gripping mechanism 3 moves along the Y-axis moving mechanism 7 to the channel opening 152, and retrieves the rack 10 from the transfer tank 30. The rack barcode scanning mechanism 4 scans and enters information. The rack 10 is moved into the rack storage hole 2142 in the liquid nitrogen storage tank 2, ensuring whole-process cold chain cryotube picking. The cryotube suction mechanism 5 retrieves the cryotube from the rack 10. The cryotube is temporarily placed in the cryotube temporary storage hole 2143. The cryotube barcode scanning mechanism 6 enters information, and then the cryotube is input into the aluminum tube 20 of the cellular turntable assembly 212 to achieve cryotube storage. The retrieval process of transfer samples is opposite to the storage process mentioned above.

The guide rail type transfer tank sample transport mechanism 9 cooperates with the upper cabin 1 and the liquid nitrogen storage tank 2 of the automated storage and retrieval device for a biological sample to achieve the serial docking function of multiple automated storage and retrieval device for a biological sample. The design improves the transfer efficiency of the transfer tank 30 and enhances the sample transfer efficiency between multiple automated storage and retrieval devices.

In a further implementation of the present disclosure, the opening mechanism 8 includes opening plate 81 that is provided therein with a magnetic attraction element. The opening plate 81 is connected to an upper end of second movable link 82. A lower end of the second movable link 82 is slidably provided in a movable frame at one end of first movable link 83 through a movable element. The other end of the first movable link 83 is hinged to support 84. The support 84 is fixed to the reference plate 15.

The second movable link 82 is further connected to lifting drive element 85 through a rotating shaft. The lifting drive element 85 is provided with limit element 851 for constraining a movement angle of the second movable link 82. The lifting drive element 85 is further provided on a support rail of the support 84 through sliding element 86. The sliding element 86 is driven by opening motor 87 to move up and down.

In a further implementation of the present disclosure, the guide rail type transfer tank sample transport mechanism 9 includes transfer tank transport mechanism 91 and lifting mechanism 92. The transfer tank transport mechanism 91 is provided at a top of the lifting mechanism 92 through transfer guide rail 93.

The transfer tank 30 enters the channel opening 152 through the lifting mechanism 92. Alternatively, the transfer tank is placed onto the transfer tank transport mechanism 91, and docked by the transfer tank transport mechanism 91 along a guide rail to another automated storage and retrieval device for a biological sample connected in series.

In a further implementation of the present disclosure, the transfer tank transport mechanism 91 includes transport housing 911 and carrier pedestal 912 that are connected vertically. The transport housing 911 is provided with support plate 9111 for placing the transfer tank 30. The carrier pedestal 912 is provided on the transfer guide rail 93.

The lifting mechanism 92 includes support member 921 and driving member 922 that are connected to a side of the liquid nitrogen storage tank 2. The support member 921 is fixed to the transfer guide rail 93 from a bottom and able to drive the transfer tank 30 to move up and down under the control of the driving member 922. Furthermore, an outer part of the lifting mechanism 92 can also be provided with a housing structure, which is connected to an outer part of the liquid nitrogen storage tank 2 as a whole.

In a specific implementation, a limit rod is provided around the support plate 9111 to accurately locate a storage position of the transfer tank 30 and prevent the transfer tank from slipping. The carrier pedestal 912 can also be provided with a battery pack, a drive assembly, a detection disc for tilt detection, a side pulley system for guidance, and an automatic alignment slider connected to a bottom through a spring.

Finally, it should be noted that the above embodiments are merely intended to describe the technical solutions of the present disclosure, rather than to limit the present disclosure. Although the present disclosure is described in detail according to the above embodiments, those of ordinary skill in the art should understand that modifications can be made to the technical solutions described in the above embodiments or equivalent replacements can be made to some of the technical features. However, these modifications or replacements do not cause the essence of the corresponding technical solutions to depart from the spirit and scope of the technical solutions of the embodiments of the present disclosure.

What is claimed is:

1. An automated storage and retrieval device for a biological sample, comprising an upper cabin and a liquid nitrogen storage tank, wherein the upper cabin is communicated with the liquid nitrogen storage tank through a storage and retrieval channel; the upper cabin is provided therein with an operation area; the operation area is provided with a rack gripping mechanism, a rack barcode scanning mechanism, a cryotube suction mechanism, and a cryotube barcode scanning mechanism, and is configured to retrieve and store samples from the liquid nitrogen storage tank in the upper cabin through the storage and retrieval channel; and the upper cabin is provided with a pressure relief member for automatically discharging a pressure of the upper cabin;
   wherein the pressure relief member comprises a squeezable pressure relief tube; and the squeezable pressure relief tube comprises a first end communicated with the operation area and a second end closed by an adjusting element, with a closing size adjusted by an adjusting bolt group;
   wherein the upper cabin comprises a cabin base plate and an outer cabin cover provided on the cabin base plate; the outer cabin cover comprises an operation chamber housing located above the storage and retrieval channel; and the pressure relief member is provided on the operation chamber housing;
   wherein the outer cabin cover further comprises an electrical control box housing provided side by side with the operation chamber housing on the cabin base plate and communicated with the operation chamber housing at a bottom;
   wherein the rack gripping mechanism, the rack barcode scanning mechanism, the cryotube suction mechanism, and the cryotube barcode scanning mechanism are provided in the operation area through a reference plate; the reference plate is located on the cabin base plate; and the reference plate and the cabin base plate are jointly provided with a storage and retrieval port corresponding to the storage and retrieval channel; and the rack gripping mechanism is located at a first side of the storage and retrieval port through a Y-axis moving mechanism; a second side of the storage and retrieval port is provided with the cryotube suction mechanism; and the rack barcode scanning mechanism and the cryotube barcode scanning mechanism are located at an end of the storage and retrieval port away from the electrical control box housing.

2. The automated storage and retrieval device for the biological sample according to claim 1, wherein the rack gripping mechanism comprises a gripper, a driving actuator, a lifting slider, and a longitudinal slide rail; the gripper is provided on the lifting slider through a connecting plate; and the lifting slider is slidably provided on the longitudinal slide rail and is connected to the driving actuator in a transmission manner; and the Y-axis moving mechanism comprises a Y-axis track and a moving carriage slidably connected to the Y-axis track; the Y-axis track is fixed to the reference plate; and the longitudinal slide rail is connected to the moving carriage.

3. The automated storage and retrieval device for the biological sample according to claim 2, wherein the cryotube suction mechanism comprises a driving motor, a vertical rod, a slider, a rotating arm, and a suction mechanism; and the suction mechanism is provided on the slider through the rotating arm; and the slider is slidably provided on a slide rail of the vertical rod and is connected to the driving motor in a transmission manner.

4. The automated storage and retrieval device for the biological sample according to claim 3, wherein the suction mechanism comprises a suction tip, a pedestal, a base, an air rod, a magnetic induction coil, and a magnetic rod; the base is connected to the rotating arm; the pedestal is connected to the base; the air rod comprises an upper end connected to the pedestal and a lower end provided with the suction tip and extending through a first through hole of the base towards a lower side of the rotating arm; and the magnetic rod comprises an upper end connected to the pedestal and a lower end extending into a second through hole of the base through the magnetic induction coil; and a liquid storage cylinder and a cooling guide tube are communicated vertically, hold liquid nitrogen, and are sleeved outside the air rod.

5. The automated storage and retrieval device for the biological sample according to claim 4, wherein the rack barcode scanning mechanism comprises a rack barcode scanning fixed frame provided on the reference plate; an upper opening of the rack barcode scanning fixed frame is provided with a rack barcode scanning upper cover plate; the rack barcode scanning upper cover plate is provided with a light source element and a barcode scanning window; and the rack barcode scanning fixed frame is provided therein with a barcode scanner, wherein the barcode scanner faces the barcode scanning window.

6. The automated storage and retrieval device for the biological sample according to claim 5, wherein the cryotube barcode scanning mechanism comprises a barcode scanning motor provided on the reference plate; the barcode scanning motor is connected to a rotating post in a driving manner; a side of the rotating post is fixedly connected to a rotary arm; and the rotary arm is provided with a barcode reader.

7. The automated storage and retrieval device for the biological sample according to claim 6, wherein the liquid nitrogen storage tank comprises a tank body and an upper cover; the upper cover comprises an upper support portion and a lower connection portion, wherein the upper support portion and the lower connection portion are integrated and respectively configured to mount the upper cabin and connect an upper opening of the tank body in a sealing manner; and the storage and retrieval channel is located on the upper cover and penetrates through the upper support portion and the lower connection portion.

8. The automated storage and retrieval device for the biological sample according to claim 7, wherein a bottom of the tank body is provided on a support seat, and four sides of the tank body are fixed by a support frame; and the upper support portion of the upper cover extends beyond an outer periphery of the lower connection portion, and is supported by a leveling alignment post provided at a top of the support frame.

9. The automated storage and retrieval device for the biological sample according to claim 8, wherein the tank body comprises an inner tank and an outer tank sleeved outside the inner tank; the inner tank is provided therein with a cellular turntable assembly; and a cryotube is stored on the cellular turntable assembly through an aluminum tube.

10. The automated storage and retrieval device for the biological sample according to claim 9, wherein a guide rail transfer tank sample transport mechanism is provided outside the liquid nitrogen storage tank; the cabin base plate and the reference plate share an extension portion beyond the upper cover; the extension portion is provided with a channel opening and located above the guide rail transfer tank sample transport mechanism; and an opening mechanism is provided on the reference plate at a side of the channel opening.

11. The automated storage and retrieval device for the biological sample according to claim 10, wherein the opening mechanism comprises an opening plate, wherein the opening plate is connected to an upper end of a second movable link; a lower end of the second movable link is slidably provided in a movable frame at a first end of a first movable link; a second end of the first movable link is hinged to a support; and the support is fixed to the reference plate; and the second movable link is further connected to a lifting drive element through a rotating shaft; the lifting drive element is provided with a limit element for constraining a movement angle of the second movable link.

12. The automated storage and retrieval device for the biological sample according to claim 10, wherein the guide rail transfer tank sample transport mechanism comprises a transfer tank transport mechanism and a lifting mechanism; and the transfer tank transport mechanism is provided at a top of the lifting mechanism through a transfer guide rail; and a transfer tank enters the channel opening through the lifting mechanism; or the transfer tank is placed onto the transfer tank transport mechanism, and docked by the transfer tank transport mechanism along a guide rail to another automated storage and retrieval device for a biological sample connected in series.

13. The automated storage and retrieval device for the biological sample according to claim 12, wherein the transfer tank transport mechanism comprises a transport housing and a carrier pedestal, wherein the transport housing and the carrier pedestal are connected vertically; the transport housing is provided with a support plate for placing the transfer tank; and the carrier pedestal is provided on the transfer guide rail; and the lifting mechanism comprises a support member and a driving member, wherein the support member and the driving member are connected to a side of the liquid nitrogen storage tank; and the support member is fixed to the transfer guide rail from a bottom and allowed to drive the transfer tank to move up and down under a control of the driving member.

14. The automated storage and retrieval device for the biological sample according to claim 11, wherein the guide rail transfer tank sample transport mechanism comprises a transfer tank transport mechanism and a lifting mechanism;

and the transfer tank transport mechanism is provided at a top of the lifting mechanism through a transfer guide rail; and a transfer tank enters the channel opening through the lifting mechanism; or the transfer tank is placed onto the transfer tank transport mechanism, and docked by the transfer tank transport mechanism along a guide rail to another automated storage and retrieval device for a biological sample connected in series.

15. The automated storage and retrieval device for the biological sample according to claim 14, wherein the transfer tank transport mechanism comprises a transport housing and a carrier pedestal, wherein the transport housing and the carrier pedestal are connected vertically; the transport housing is provided with a support plate for placing the transfer tank; and the carrier pedestal is provided on the transfer guide rail; and the lifting mechanism comprises a support member and a driving member, wherein the support member and the driving member are connected to a side of the liquid nitrogen storage tank; and the support member is fixed to the transfer guide rail from a bottom and allowed to drive the transfer tank to move up and down under a control of the driving member.

* * * * *